(12) United States Patent
Durón

(10) Patent No.: US 6,257,064 B1
(45) Date of Patent: Jul. 10, 2001

(54) WAVE SPEED BRIDGE DAMAGE DETECTION METHOD

(75) Inventor: Ziyad H. Durón, Claremont, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 09/342,015

(22) Filed: Jun. 28, 1999

(51) Int. Cl.⁷ .................................................. G01N 29/18
(52) U.S. Cl. .................................................. 73/598; 73/594
(58) Field of Search ........................ 73/598, 594, 597, 73/12.01

(56) References Cited

U.S. PATENT DOCUMENTS

| | | | | |
|---|---|---|---|---|
| 5,275,051 | * | 1/1994 | De Beer ................................ | 73/598 |
| 5,307,679 | * | 5/1994 | Ross ...................................... | 73/597 |
| 5,996,413 | * | 12/1999 | Iyer et al. ............................. | 73/598 |
| 6,105,430 | * | 8/2000 | Kepler et al. ........................ | 73/594 |

OTHER PUBLICATIONS

Aktan, E., Helmicki, A. Brown, D. , "Global Bridge Condition Assessment, National Test Bridge HAM–561–0683, Peer Review Panel Presentation Nov. 18, 1996," University of Cincinnati Infrastructure Institute.

* cited by examiner

Primary Examiner—John E. Chapman
(74) Attorney, Agent, or Firm—Derrick Michael Reid

(57) ABSTRACT

An impact test method excites a bridge by an impact hammer at an impact point to create impact waves traveling through the bridge toward distal and proximal ends of the bridge where transient responses are measured in time reference to impact excitation. Time delays from an impact trigger time referenced to the reception of the transient responses over respective distances traveled by the impact wave provide wave speed indices that can be used to indicate structural change or damage of the bridge when compared to pre-damaged wave speed indices.

13 Claims, 3 Drawing Sheets

WAVE SPEED TEST - PROXIMAL END RESPONSE

WAVE SPEED TEST - DISTAL END RESPONSE

FIRST ARRIVAL RESPONSES AND FORCE PULSE

WAVE SPEED ESTIMATES

WAVE SPEED BRIDGE DAMAGE DETECTION METHOD

STATEMENT OF GOVERNMENT INTEREST

The invention was made with Government support under contract No. F04701-93-C-0094 by the Department of the Air Force. The Government has certain rights in the invention.

FIELD OF THE INVENTION

The invention relates to the field of structural damage detection. More particularly, the invention relates to damage detection of highway bridges and superstructures.

BACKGROUND OF THE INVENTION

In recent years there have been numerous attempts to develop damage detection and condition assessment capabilities that could be used to mitigate hazards associated with potential failure of bridges, as well as other large civil structures. The need for the development of these techniques is motivated by the estimated tens of billions of dollars needed to repair or retrofit these structures. These efforts have been based, in part, on modal testing techniques that have attempted to identify critical response indices sensitive to changes in structural condition or integrity. Most approaches that have been demonstrated to show sensitivity to changes in structural condition have required extensive field measurements often requiring bridge closure to traffic. Early work focused on modal indices indicating changes in modal resonant frequencies as an indicator of potential damage. However, recent work has revealed these modal indices to be largely inadequate due to the weak correlation between damage and measured frequency shifts. The use of damping has also not provided reliable indications of damage in most cases. Changes in mode shape geometry, that is, changes in the vibrating shape of the structure at a resonant frequency, have shown greater sensitivity to damage but lack practical accuracy. Other more sensitive methods of using modal parameters to assess changes in structural condition have been developed, including the use of flexibility, strain energy, and mode shape curvature, for example. These approaches do not, however, provide a quick and accurate description of the overall condition of the bridge that might enable prompt inspections and early corrective actions.

Ambient measurements for a particular bridge, the Seymour Bridge of Cincinnati Ohio, have been made to provide initial characterization of the bridge for baseline comparisons. This particular bridge is approximately 40.0 m long and 12.0 m wide from the proximal bridge end to the distal bridge end, with 3.7 m wide traffic lanes and 2.4 m wide sidewalks for pedestrian traffic. Two bridge piers provide support for the deck located 12.0 m inward from abutments at the proximal and distal ends. The upper deck surface is a composite design made of 6.4 cm of asphalt surface over a 16.5 cm thick concrete slab and supported by six steel I-Beams girders all of which extend along the length of the bridge. The exterior beams under the sidewalk edges are W21×73 and the interior beams are W27×94. Lateral bracing is provided by intermediate cross frames that are spaced approximately 3.67 m apart. The bracing used is L section 3×3×5/16 welded with 0.64 cm fillet welds to the beam webs. Ambient acceleration responses are acquired on the bridge monitoring locations using accelerometers mounted on small aluminum blocks bolted to a leveling platform that stands off the deck surface on three leveling screws. Each mounting block contains at least one accelerometer oriented in the vertical direction, but may also contain a second accelerometer oriented in the transverse direction. The accelerometer platform can be simply placed on the upper deck surface and a bubble level used to ensure true vertical and transverse orientation for each measurement axis. No bonding agents or adhesives are required for accelerometer placement on the deck surface. Typical ambient measurement locations are spaced apart, such as, at 3.0 m intervals along the length of the bridge and at 2.6 m along the width, for a total of 90 monitor locations during testing. Bi-axial acceleration measurements were oriented along longitudinal through-traffic and transverse cross-traffic directions at each location. During the ambient tests, it is necessary to locate two fixed measurement locations that are later utilized as reference measurements in the computation of the frequency response. Although ambient responses may contain large transient spikes corresponding to vehicular traffic passing under the bridge, these spikes do not typically exceed a 10.0 mg peak. Transient components of the ambient responses usually decay within one second. Random vibration levels present in the responses are bounded by a 1.0 mg peak, and accurate levels can be determined to be less than a 0.1 mg peak. Power spectral estimates show that although the responses along the transverse directions were substantially smaller in magnitude, sufficient signal quality was present for correlation with vertical measurements. Ambient testing can provide power spectral measurements that are used to identify modal frequencies and shapes, such as resonance frequencies at 7.1 Hz and 8.2 Hz for the Seymour Bridge.

Analyses of the ambient responses revealed that, although changes in bridge modal amplitude response characteristics could be measured and perhaps attributed to the presence of damage in the bridge, these changes were limited to the order of 10%. In the context of measurement uncertainties that may approach 10%, the sensitivity of this modal amplitude index appears inadequate. During the conduct of the ambient tests, noticeable and measurable differences in wave arrival times can be observed on the bridge from traffic induced transient responses. However, wave speed indices that might provide some correlation to changes in structural condition on the steel stringer bridge, have not been used to reliably determine bridge damage. These and other disadvantages are solved or reduced using the invention.

SUMMARY OF THE INVENTION

An object of the invention is to provide a method for testing the structural integrity of large structures.

Another object of the invention is to provide a method for testing for damage to a bridge over bridge segments.

Yet another object of the invention is to provide a method of impact and wave speed measurements for the detection of damage to a bridge.

The present invention is directed to a wave speed based diagnostic testing method that provides a non-intrusive method of monitoring a structure with a wave speed measurement used as an index for providing sufficient sensitivity to changes in structural condition without requiring lengthy test times and complicated test procedures. The method provides a quick and accurate description of the overall condition of the bridge and can be used to monitor the overall structural integrity of the structure and perhaps prompt inspections and early corrective actions. The method enables accurate characterization of bridge structural conditions, using instrumentation and test procedures that to do not require bridge closure to traffic. In addition, the method provides the added safety of allowing the conduct of the test to be performed on the underside of the bridge deck, protecting both instrumentation and operator from passing vehicular traffic.

The method is based on the accurate identification of first arrival times of an impact wave traveling through a structure arriving at monitoring points. The impact wave can travel, for example, through girders from the impact point. A propagation mechanism of the impact wave is insensitive dispersion and avoids the complication of detailed modal surveys and interpretation of results. The method is readily practicable to implement. The method requires a minimum of one accelerometer for monitoring an impact wave and one calibrated impact hammer for creating the impact wave. Standard computer and communications technologies are used to acquire and process the measured responses.

In the preferred form, the invention is directed to a wave speed based field test method that can be used to evaluate the structural condition of a bridge, such as a steel stringer bridge. The method involves the monitoring of induced responses at the monitoring points, such as the ends of the support girders, from an impact applied at a known location along the bridge, such as upon a girder. Monitoring responses, such as girder end responses, are acquired using accelerometers and a calibrated or instrumented hammer providing the impact. Accelerometers are preferably placed at each end of a support girder and the hammer is used to impact the girder at a predetermined impact location. For each impact location, a series of a plurality of data sets can be acquired to ensure statistical accuracy with high coherence in results. Wave speed estimates are based on measured arrival times and distances between impact and measurement locations. Large changes in a wave speed index, approaching 40%, indicate a high probability that a change in the structural condition exists in the bridge, indicating possible damage. The method can be used to determine, not only distinct damage to the structure, but also modest structural changes. For example, modest change may occur due to continued use and age, whereas significant damage may occur due to a significant event, such as a vehicular impact, earthquake, or severe weather event. The method has been demonstrated on a steel stringer bridge, and can be performed by a single field trained technician. The resulting wave speed index demonstrated a greater sensitivity to the induced damage in the bridge than did the indices based on modal properties, such as, modal frequencies, changes in mode shapes, and flexibility.

The preferred method can be used to obtain wave speed measurements from impact points to monitoring points at differing times and at differing locations. In a first preferred method, wave speed measurements are taken from a first impact point to a monitoring point at an initial time, and at a subsequent time, to determine if the bridge has experienced damage during the period between the initial time and subsequent time. For example, the time between the time of construction and a later event time. In a second preferred method, two wave speed tests are concurrently performed at the same time by two respective impact events. The two wave speed tests can be conducted from a first impact point to a distal point over a first segment of the bridge having a first wave speed measurement, and conducted from a second impact point to a proximal point over a second segment of the bridge having a second wave speed measurement. The first and second wave speed measurements can be compared to determine which one of the first and second segments has probable bridge damage. These and other advantages will become more apparent from the following detailed description of the preferred embodiment.

DETAILED DESCRIPTION OF THE PREFERRED EMBODIMENT

Figure 1:
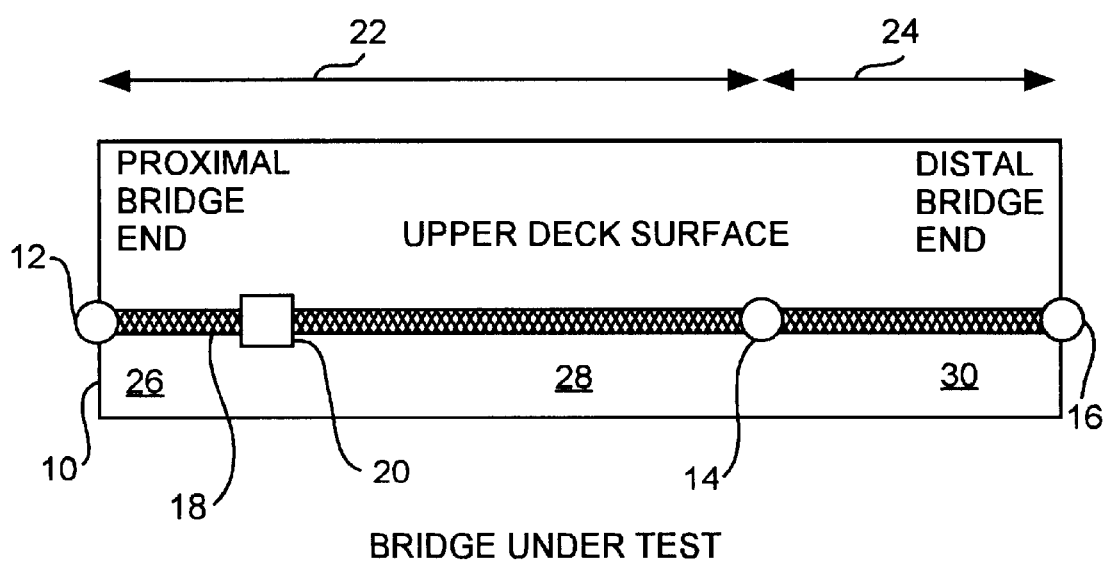
FIG. 1 is an overhead view of a bridge under test.

An embodiment of the invention is described with reference to the figures using reference designations as shown in the figures. Referring to FIG. 1, an exemplary bridge 10 under test is shown. During testing, impact waves arrive at a proximal end response location 12 from an impact location 14. Impact waves also arrive at a distal end response location 16 also from the impact location 14. Impact waves travel along the structure, such as along and through a girder 18 having a damage location 20. The exemplar girder 18 extends from the proximal bridge end 26, under an upper deck surface 28, to the distal bridge end 30. The bridge 10 may be a steel stringer bridge such as the Seymour Avenue Bridge of Cincinnati Ohio.

The impact test method preferably involves monitoring acceleration responses at each of the ends 26 and 30 on the support girder 18 during impact at the single impact location 14 along the girder 18. Once the accelerometers are placed, a location along the interior of the girder length is selected as the impact location. The distances between the impact point and the accelerometer locations are measured and used to determine the wave speed estimates. The impact test method allows for the generation of an impact wave in the form of a force pulse that propagates along the support girder 18 away from the impact point 14 and toward each girder end 12 and 16. For each impact, the force pulse that is typically generated by an impact hammer at the impact point 14, is used as a trigger for acquisition of transient response signals that are accelerometer responses at each girder end. The response signals are digitized using computer controlled data acquisition. Acquisition can capture pre-impact, first wave arrival, and subsequent transient decay response at each end. A series of impact tests can be performed to ensure adequate statistical quality and repeatability in wave speed estimates.

The wave speeds, measured in this manner, do not represent a local material property, but instead are considered as global parameters associated with the condition of the bridge 10 at the time of test. The wave speed estimates are examined for large changes in value based on comparisons between pre-damage and post-damage impact test results at differing times, or between differing segments of the bridge at the same time. Initial time wave speech measurements can be taken at a time of construction when the bridge is without damage, and can be taken at a later time, when the bridge may be damaged. Comparison between the wave speed measurements between the initial and later times may indicate bridge damage with large variations in wave speed data or indicate a lack of damage when the wave speed data has not significantly changed from the initial time to the later time. Wave speed measurements can also be taken concurrently over different segments of the bridge at the same time. Wave speed measurements through a first segment between the impact point 14 and the proximal end 26 can be compared to wave speed measurement through a second segment between the impact point 14 and the distal end 30.

The first and second wave speed measurements for the first and second segment can be compared to provide an indication as to which of the two segments has probable bridge damage.

Figure 2A:
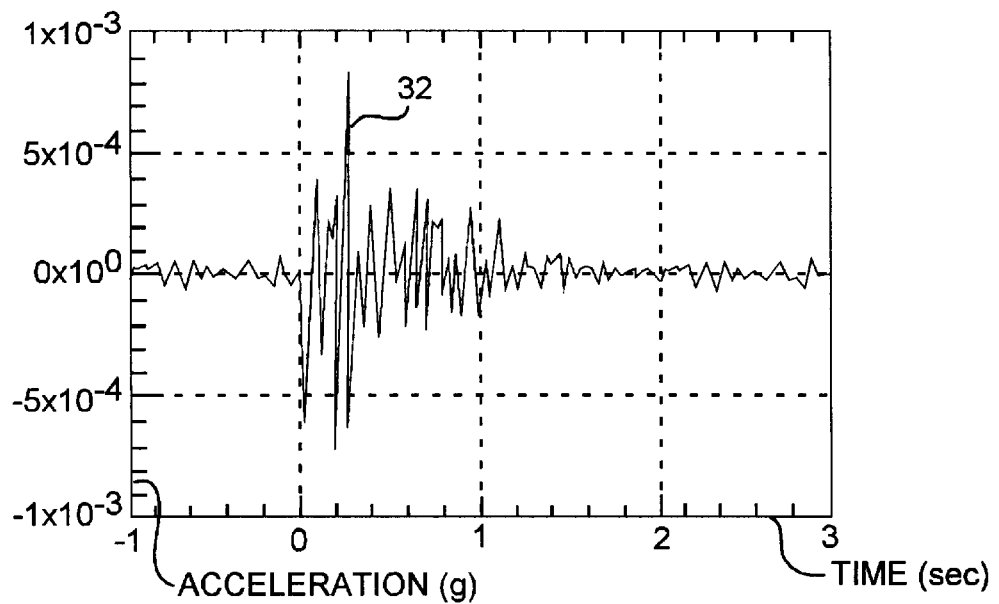
FIG. 2A is a wave speed plot at a proximal bridge end.
Figure 2B:
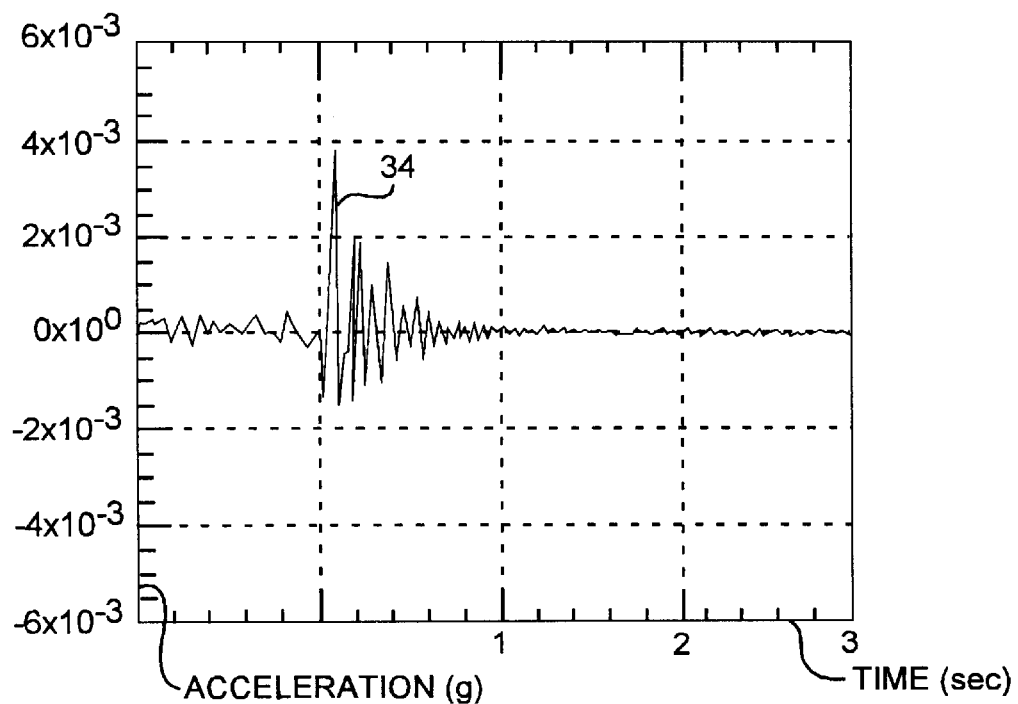
FIG. 2B is a wave speed plot at a distal bridge end.

Referring to FIGS. 1, 2A, and 2B, exemplar samples of measured transient responses 32 and 34 are shown for the respective proximal end 26 and the distal end 30. The relative transient response amplitudes are consistent with the proximity of the measurements to the impact location, with the distal end response indicating larger amplitudes by almost a factor of six. Wave speed estimates are made on the basis of identifying first arrival times at each end location from the time of impact divided by measured or known distances between impact point and response monitoring positions over respective bridge segments. The analysis procedure is based on sensing for transitions from ambient or pre-event conditions to actual wave arrival. The arrival time is preferably determined by setting a threshold level above the ambient noise levels. The wave speed measurements, as shown, indicate a time zero when the response signals exceed a threshold level at the beginning of the transient responses 32 and 34.

Figure 3:
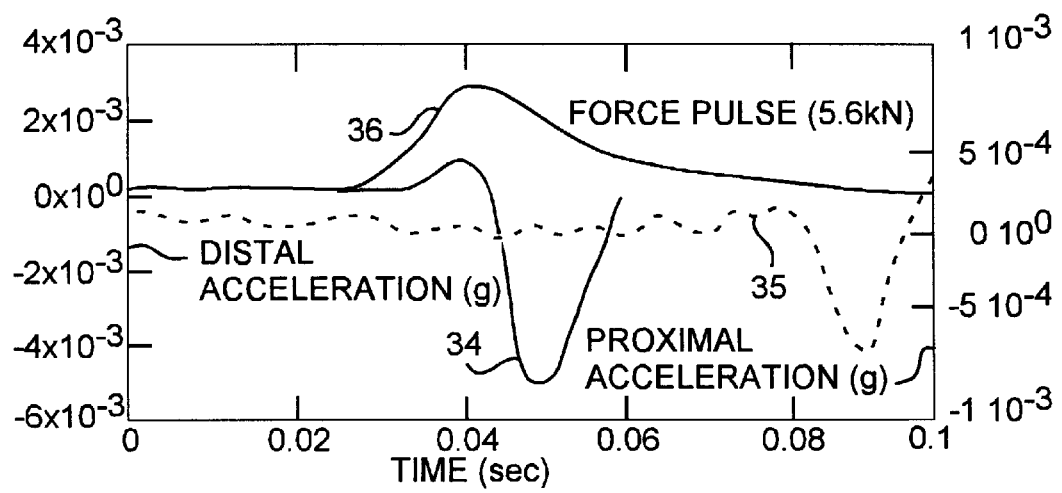
FIG. 3 is a plot of a force pulse and resulting first arrival responses.

Referring to all of the Figures, and more particularly to FIG. 3, distal and proximal wave speed traces 34 and 35, respectively, and impact trace 36, are acquired at a predetermined sampling rate, for example, between 250 and 10,000 samples per second, preferably 1000 samples per second. The desired resolution available in the measured responses provides an ability to assign a single arrival time for the transients at each end of the girder 18. Typically, the wave speed is determined when the measured response exceeds the predetermined threshold while the response is being sampled at the predetermined sampling rate. Identifying the initial time for the force pulse 36 is practical because ambient force levels are well below the impact force level 36 at the impact point 14. The same may not be true for the acceleration response measurements 34 and 35. Excessive ambient response levels present in the data for the impact tests may render wave speed estimates unreliable. When conducting the wave speed tests, the presence of traffic induced vibration levels may almost entirely mask the arrival time of the transient response wave, increasing the uncertainty associated with any subsequent wave speed estimate. Hence, the wave speed test method is preferably conducted in the absence of traffic to prevent false measurements when traffic induced measurements exceed the predetermined threshold level.

The exemplar impact force 36 and response signals 34 and 35 are shown to estimate first wave arrival times during wave speed tests. The baseline signals at time zero indicate ambient condition from pre-impact event to wave arrival at each end, the distal end 34, the proximal end 35, in view of the impact force 36. In order to better define the first arrival times and improve the accuracy of the resulting wave speed estimates, the measured responses 34 and 35 may be interpolated to enhance resolution in the time records. In this case, interpolated responses were obtained with 0.1 milli second resolution. Although first arrival estimates can be made with less uncertainty from the interpolated responses, the relatively small ambient levels prior to impact contribute significantly to the accuracy in the estimates.

Figure 4:
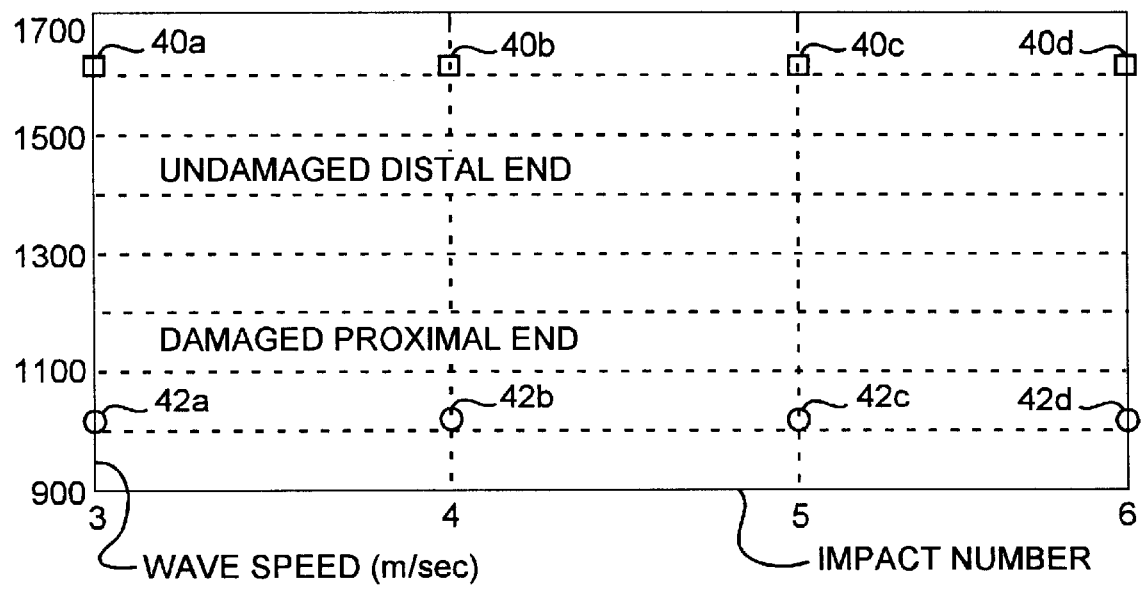
FIG. 4 is a plot of wave speed estimates.

Referring to all of the Figures, and more particularly to FIG. 4, wave speed results are obtain from the impact tests. Indicated are multiple wave speed estimates 40a, 40b, 40c and 40d for the distal end, and estimates 42a, 42b, 42c and 42d for the proximal end, of measure wave speed taken from four of the six impacts on the bridge from both ends of the girder. Average wave speeds measured across the undamaged portion of the girder 18 was 1621 m/sec, and speeds across the damaged portion averaged 1024 m/sec, corresponding to a significant 40% change in wave speed between the damage and undamaged ends of the support girder. Hence each of the first and second bridge segments between the impact point 14 and the monitoring points 12 and 16, respectively have different wave speed measurements. The variation in wave speed estimates among a series of impact tests performed for both damaged and undamaged segment is small, for example, less than 5%. Reduced wave speed estimates would be expected from propagation around a crack in a steel beam indicating smaller values measured across the segment of damaged proximal end 26.

To verify the wave speed estimates for the undamaged end, impact data acquired during previous initial time impact tests can be conducted again at a subsequent time on the same bridge after inducing damage 20. The wave speed measurements at the initial time can be compared to wave speed measurements at the subsequent time. During the initial impact tests, responses from a single impact along the same support girder tested during the wave speed tests can be acquired under undamaged conditions. Wave speed estimates from the prior impact tests, without induced damage in the bridge, were found to be consistent with those obtained over the undamaged bridge segment during subsequent time wave speed tests. Also, wave speed estimates through the damaged segment showed significant changes over the same segment prior to induced damage and at the initial time. Effects of dispersion on the arrival time estimates were observed to be minimal during the wave speed tests, indicating that the mechanism for the first arrival is not dispersive. The change in the wave speed index, measured to be about 40%, provides a clear indication of a change in the structural condition in the bridge further indicating damage induced in the bridge. Hence, the wave speed test not only indicates damage, but also indicates in which segment the damage is located.

Results from the wave speed impact tests conducted along the damaged support girder may be realized by a diagnostic field test method. The wave speed test method is preferably used on steel stringer bridges and should be repeated for each of the support girders in the bridge. The preferred wave speed test method consists of monitoring transient responses at the girder ends due to an impact at another known interior location on the girder. A minimum of two impact locations on the girder is preferred in the unlikely event an impact location coincides with a damage location. Also, multiple impacts at each location may also be preferred to ensure statistical accuracy with high coherence. Data can then be transmitted and processed off-site to a database from which an alert could be issued tagging the girder for detailed inspection based on a significant variation in wave speed index. Minimum requirements for instrumentation include accelerometers and a calibrated impact device. Data acquisition and transmittal to the database are easily achieved with modern computer and communication technology.

To minimize the effort required during post-processing and to enhance the interpretation of the test results, impact testing is preferably conducted only during periods of no traffic in the vicinity of the bridge. Although not a necessary condition for the conduct of these tests, traffic induced ambient vibration levels tend to obscure the transition from ambient to transient response behavior. For each triggered acquisition, an impact time period interval elapses. The impact time interval is an interval that is sufficient to capture the arrival of the initial transient wave response, the transient response, and a return to pre-event ambient conditions. The impact time interval may be only several seconds, such as eight seconds. The use of the wave speed index as an indicator of a change in the structural condition can also provide adequate sensitivity to damage induced in the bridge. The relatively large change in the wave speed index that approach 40%, is a significant change in the wave speed index and suggests a significant change in the structural condition of the bridge. A 40% change is suitable for diagnostic field test procedures and well suited for testing steel stringer bridges in which responses at each end of the support girders are obtained from impacts at known locations on the bridge deck.

The method can be applied to two basic ways. A wave speed test can be conducted upon bridge construction and that data saved for later reference. A subsequent retest provides a subsequent wave speed measurement that is compared to the original wave speed test. The difference in the initial and subsequent wave speed measurements provides an indication of probable bridge damage since the initial test. The wave speed test can be conducted between the impact point and the two proximal and distal points to provide two wave speed measurements. A difference between these two wave speed measurements may indicate that the bridge has experienced a significant change in structural condition, or has experienced severe damage since the initial test. This difference also may be used to indicate in which bridge segment the damage or structural change is located, that is, the segment between the impact point to proximal point, or, the segment between the impact point and the distal point, whichever segment has the highest wave speed change since the initial wave speed measurements. The wave speed test can also determine which segment has the greatest statistical variation from the remaining segments at any point in time. In this way, the wave speed test can be used to not only indicate if the bridge is damaged, but also used to indicate where in the structure the damage is located. Those skilled in the art can make enhancements, improvements and modifications to the invention, and these enhancements, improvements and modifications may nonetheless fall within the spirit and scope of the following claims.

What is claimed is:

1. An impact test method for determining damage of a structure including girders, the method comprising the steps of, impacting the structure at a first test time at an impact point along the structure to create a first impact wave at the impact point, the first impact wave propagates through the girders away from the impact point to become a first transient response at a monitoring point, measuring the first transient response at the monitoring point, determining a first wave speed of the first impact wave traveling from the impact point to the monitoring point becoming the first transient response, repeating the impacting, measuring and determining steps at a second impact point at second test time to create a second impact wave and a respective second transient response for determining a second wave speed, the first test time being after construction of the structure, the second test time being after the first test time, the first and second transient responses are within a resonant frequency range of the structure, and comparing the first wave speed to the second wave speed to determining a change in the structure indicating induced damage between the first test time and second test time.

2. The method of claim 1 wherein the first and second impact points are the same impact point.

3. The method of claim 1 wherein the first and second monitoring points are the same point.

4. The method of claim 1 wherein a change of greater than 5% between the first and second wave speeds indicate damage in the structure.

5. The method of claim 1 wherein the structure is a stringer bridge formed by the girders and the first and second impact waves travel through the girders along the bridge.

6. An impact test method for determining damage of a structure including girders, the method comprising the steps of, impacting the structure at an impact point to create an impact wave at the impact point, the impact wave propagates through the girders towards a first monitoring point and a second monitoring point to respective become a first transient response and a second transient response, measuring the first transient response at the first monitoring point and measuring the second transient response at the second monitoring point, the first and second transient responses are within a resonant frequency range of the structure, determining a first wave speed of the impact wave traveling from the impact point to the first monitoring point, determining a second wave speed of the impact wave traveling from the impact point to the second monitoring point, and comparing the first wave speed to the second wave speed to determine a change between the first and second wave speeds to indicate the damage.

7. The method of claim 6 wherein the structure is divided into first and second segments trough which the impact wave travels respectively to the first and second monitoring point, and wherein a difference between the first and second wave speeds indicates which one of first and second segments is damaged.

8. The method of claim 7 wherein the structure is a stringer bridge formed by the girders and the impact wave travels through the girders along the bridge to the first and second monitoring points.

9. The method of claim 7 wherein the measuring step comprises the steps of, placing accelerometers at the first and second monitoring points, sensing for the start time at the creation of the impact wave, sampling the accelerometers to record the first and second transient responses, determining when the first and second transient responses exceed predetermined threshold to respectively determine first and second arrival times of the first and second transient responses, determining the first and second time delay between the start time and the respective first and second arrival times, and computing the first and second wave speeds by dividing first and second distances from the impact point respectively to the first and second monitoring points by the first and second arrival times, respectively.

10. An impact test method for determining damage of a structure including girders, the method comprising the steps of, impacting the structure at a first impact point to create a first impact wave at the first impact point, the first impact wave propagates through the girders towards a first monitoring point to become a first transient response, and measuring the first transient response at the first monitoring point, impacting the structure at a second impact point to create a second impact wave at the second impact point, the second impact wave propagates through the structure towards a second monitoring point to become a second transient response, the first and second transient responses are within a resonant frequency range of the structure, measuring the second transient response at the second monitoring point, determining a first wave speed of the first impact wave traveling from the first impact point to the first monitoring point, determining a second wave speed of the impact wave traveling from the second impact point to the second monitoring point, and comparing the first wave speed to the second wave speed to determine a change in the structure indicating the damage.

11. The method of claim 10 wherein, the impacting, measuring and determining steps are repeated a plurality of times for determining a plurality of first and second wave speeds from a respective plurality of first and second impact waves, and the comparing step comprises the steps of, averaging the plurality of first and second wave speed, and comparing the average of the plurality of first wave speeds to the average of the plurality of second wave speeds for determining the change in the structure indicating damage of the structure.

12. The method of claim 11 wherein, the plurality of the first impact waves travel through a first segment of the structure between the first impact point and first monitoring point, the plurality of the second impact waves travel through a second segment of the structure between the second impact point and second monitoring point, and the comparison further indicates which of the first and second segments of the structure is damaged.

13. The method of claim 11 wherein the first and second impact points are the same impact points.

* * * * *